(12) United States Patent
Hechinger

(10) Patent No.: US 7,790,928 B1
(45) Date of Patent: Sep. 7, 2010

(54) THERAPEUTIC DIMETHYL SULFOXIDE (AKA DMSO) COMPOSITIONS AND METHODS OF USE

(76) Inventor: Albert Raymond Hechinger, c/o Natural Health Producst: 12333 1/2 Washington Blvd., Los Angeles, CA (US) 90066-5525

( * ) Notice: Subject to any disclaimer, the term of this patent is extended or adjusted under 35 U.S.C. 154(b) by 1066 days.

(21) Appl. No.: 11/387,124

(22) Filed: Mar. 23, 2006

Related U.S. Application Data

(60) Provisional application No. 60/675,058, filed on Apr. 25, 2005.

(51) Int. Cl.
*C07C 317/00* (2006.01)
(52) U.S. Cl. .................................................. 568/27
(58) Field of Classification Search .................... 568/27
See application file for complete search history.

(56) References Cited

U.S. PATENT DOCUMENTS

| | | | | |
|---|---|---|---|---|
| 4,296,104 | A * | 10/1981 | Herschler | 424/679 |
| 5,401,514 | A * | 3/1995 | Juch et al. | 424/465 |
| 5,980,875 | A * | 11/1999 | Mousa | 424/70.11 |
| 2003/0022843 | A1* | 1/2003 | Wu et al. | 514/23 |

FOREIGN PATENT DOCUMENTS

JP 56158715 A * 5/1980

* cited by examiner

*Primary Examiner*—Johann R Richter
*Assistant Examiner*—Ali Soroush

(57) ABSTRACT

The use of honey, and other sugar compositions, with pharmaceutical compositions containing DMSO is disclosed. The result is a reduction in the undesirable side effects normally associated with the application of DMSO compositions, enhancement of the desired physiological effects produced by DMSO compositions, and other benefits not present with the use of DMSO alone, and/or in conjunction with other additives.

10 Claims, No Drawings

THERAPEUTIC DIMETHYL SULFOXIDE (AKA DMSO) COMPOSITIONS AND METHODS OF USE

This application claims the benefit of Provisional Patent Application Ser. No. 60/675,058 filed Apr. 25, 2005.

BACKGROUND OF THE INVENTION

The present invention relates to pharmaceutical compositions containing DMSO for administration to human or other animal subjects. More specifically, it relates to new DMSO formulations containing a substance which enhances the effectiveness of DMSO, reduces undesirable side-effects usually created by the use of DMSO and makes almost all DMSO compositions more appealing to users.

Dimethyl Sulfoxide (DMSO) is a versatile substance that has numerous pharmaceutical and non-pharmaceutical uses. It is widely used throughout the world for treating humans and animal subjects. Its use has been proven to reduce inflammation, stop pain, and promote the healing of tissue.

As Described in U.S. Pat. No. 3,549,770, No. 3,740,420, and No. 3,790,682, incorporated herein by this reference, DMSO is an active agent in relieving the signs and symptoms of numerous body disorders, including accelerating the healing of certain injured body tissues and in relieving the signs and symptoms of anxiety.

U.S. Pat. No. 3,551,554, No. 3,711,606 and No. 3,743,727, incorporated herein by reference, describe how DMSO is effective to enhance tissue penetration of other substances, especially other physiologically active agents. DMSO can thus be added to a variety of pharmaceutical compositions to accelerate assimilation into body tissue. In some instances this means that smaller doses can be administered when DMSO is used.

Yet, despite their many benefits, DMSO compositions are sometimes passed over in favor of other pharmaceutical compositions even in instances where DMSO would be the most effective pharmaceutical agent. This is because many subjects suffer from one or more side-effects when treated with DMSO. In some cases, the side-effects are so pronounced that subject or physician will forego the use of DMSO in favor of a less effective therapeutic agent.

Several undesirable side-effects have been observed to result from administration of DMSO. The most frequently occurring are adverse skin reactions, and/or minor irritation, malodorous breath and foul taste. These are the side effects which my invention reduces and/or eliminates.

The adverse reactions caused by DMSO are well documented. At page 356 of the standard reference Contact Dermatitis by Alexander A. Fisher, M. D. (2nd Ed., 1973), dimethyl sulfoxide (DMSO) is listed as a primary urticariogen (skin irritant). Volume 141 of Annals New York Academy of Sciences includes several articles describing the undesirable side-effects attributed to DMSO. These include articles by Goldman, et al. at pages 429, 433-35; Sulzberger, et al. at pages 439-40; Brown at pages 500-501; and several others.

The magnitude of the malodorous breath problem is so large that, in some instances, it has been claimed that hospitals have had to isolate wards where DMSO is administered from the central air conditioning system. Skin irritations from topically applied DMSO have been so great that a substantial number of patients refuse treatment. Bad breath is especially prevalent when DMSO is administered orally.

SUMMARY OF THE INVENTION

Specific DMSO compositions and methods of application have now been discovered. Use of such compositions expands the acceptability of DMSO by eliminating or reducing undesirable side-effects, and, in addition to reducing the undesirable side effects, the new DMSO compositions and methods of use are observed to provide new therapeutic effects and beneficial uses.

More specifically, it is found that when DMSO and honey are both administered to epithelial regions of a human or other animal subject, expected adverse skin reactions, malodorous breath and foul taste are substantially reduced. In many cases they are entirely eliminated.

Furthermore, honey is discovered to potentiate DMSO in certain instances. It appears that a DMSO composition containing honey enhances the therapeutic effects of the DMSO, as opposed to the effects when no honey is incorporated to the DMSO solution. The presence of honey reduces discomfort resulting from topical application of DMSO compositions and it appears that it may further enhance penetration. Honey is very symbiotic as an adjunct in solution with DMSO as honey is a curative agent in its own right, as well as a skin emolument. Honey not only moisturizes skin, it is also an anti-bacterial agent. Honey has also been proven to further enhance wound healing of tissue.

It has also been discovered that certain DMSO formulations, which contain honey, are at times effective, or more effective, in treating diseased finger and toe nails, for softening cuticle to be removed from finger and toe nails, and for softening epidermal thickenings to ease removal.

It is therefore an object of this invention to provide pharmaceutical compositions and methods to allow the application of DMSO to a human or other animal subject without creating adverse skin reactions, malodorous breath or foul taste. In this regard, honey greatly reduces the bad taste, and the aftertaste of orally administered DMSO therapies.

An additional object of this invention is to enhance the curative effects of the administration of DMSO, by the addition of measured amounts of honey, over that which is derived from the administration of DMSO alone. These enhancements are due, in part, to the curative abilities of honey, its moisturizing and skin softening abilities, all of which have been well documented over many years. Please see the references at the end of this application.

These and other objects, advantages and features of the present invention will be apparent from the following detailed description.

It is also contemplated that a blend of sugars, i.e. fructose, sucrose and glucose may also be utilized to help alleviate some of the undesirable side effects of the administration of DMSO alone. Compositions of these sugars may provide some benefit, however they are not nearly as effective as is honey.

DESCRIPTION OF PREFERRED EMBODIMENTS

The side-effects which have long hindered the use of DMSO as a therapeutic agent are quite surprisingly eliminated when honey is administered with formulations containing DMSO. Even small amounts of honey are beneficial in reducing histamine release, burning and itching, localized dermatitis, drying, and potential cracking of the skin, unpleasant breath odor, after-taste, headache and nausea in subjects receiving dermally administered DMSO compositions.

The bad taste, and aftertaste, are greatly reduced when honey is mixed with the DMSO for orally administered dosages.

Honey is an especially excellent inhibitor of the side-effects, because it is a naturally occurring substance, is non-toxic, and animal subjects are quite tolerant of its presence. It thus can be used with almost any pharmaceutical composition containing DMSO, without fear of toxic effects. Add to these, honey's own curative effects and it becomes clear why honey makes such an excellent additive and adjunct to DMSO therapy and usage. All of the reasons why honey is effective from reducing and eliminating the above listed undesired side-effects is not fully understood. It appears, however, that the honey inhibits or prevents the production of undesirable DMSO metabolites. Honey also has distinct germicidal properties in its own right. [See references at end supporting healing benefits of honey].

In the case of the breath odor problem, it is known that dimethyl sulfide is a minor metabolite of DMSO and that it is expired through the lungs causing malodorous breath and foul taste. Honey possibly prevents the breakdown of DMSO to dimethyl sulfide. Supporting laboratory experiments show that DMSO will decompose to dimethyl sulfide when heated in a test tube. It may appear that, when honey is added, and the experiment repeated, no dimethyl sulfide will be detected. Honey also has a sweet taste, which tends to negate the taste of the DMSO. Honey has also been proven effective in promoting wound healing and thus, its combination with DMSO, which also promotes the healing of tissue, speeds and further helps to assure healing. This is especially true in the case of open wounds and burns.

Similarly, the adverse skin reaction, such as histamine wheal and flare may be the result of an attack by the dimethyl sulfide molecule against mast cells in the subcutaneous layer of skin to which DMSO is applied topically. Honey's blocking of DMSO breakdown to dimethyl sulfide would thus account for the observed antiurticariogenic effectiveness in reducing adverse skin reactions caused by DMSO. Additionally, the nutritive and moisturizing effects of honey may also assist in preventing most, and sometimes all, of the irritation which occurs when DMSO is applied topically without honey.

DMSO is a known penetration enhancer for chemical agents having a molecular weight less than about 8,000, administered to intact body membranes. It is also found to enhance the penetration of higher molecular weight substances, such as enzymes, that are administered to stressed membranes including membranes that are inflamed, are scarified or have been subjected to severe osmotic stress. In both situations, the inclusion of honey may also improve pharmaceutical effectiveness and, in some instances, make it possible to reduce the dosage administered.

Honey can be administered with DMSO to produce the same physiological effects attributed to DMSO compositions administered without honey. For example, honey can be administered with DMSO to an area of tissue inflammation in an amount effective for relieving signs and symptoms of inflammation, to a subject suffering from pain in an amount effective to relieve pain, to a subject suffering from abnormal muscle contractions in an amount effective to promote muscle relaxation, to a subject suffering from symptoms of vascular insufficiency in the blood and lymph circulatory system in an amount effective to relieve symptoms of vascular insufficiency.

Treatment with effective amounts of DMSO and honey can also relieve signs and symptoms of a burn, can promote healing of a skin graft area following a transplant, and can relieve signs and symptoms of respiratory distress. When DMSO is given with honey to subjects having joints with arthritic signs and symptoms in an amount effective to relieve signs and symptoms of arthritis, to subjects suffering from tissue damage in an amount effective to promote the repair of tissue damage, or to mammalian subjects suffering from signs and symptoms of anxiety in an amount effective to relieve signs and symptoms of anxiety, improvement in subjects' conditions may be observed.

It has also been found that certain compositions, containing both DMSO and honey, have medical benefits not produced by compositions containing DMSO or honey alone. As one example, it is found that DMSO, administered with honey, will repair or remove abnormal, dead, or diseased tissue more readily than with just DMSO, or honey alone. DMSO-honey compositions can thus be used to treat interstitial cystitis or connective tissue diseases such as progressive systemic sclerosis. Honey and DMSO have both, alone, been proven to promote wound healing and, by combining these two products of nature, a more symbiotic relationship is established, whereby the sum of the benefits of the two are greater than the total derived from either alone.

DMSO-honey, compositions can also be administered to benefit diseased finger and/or toe nails of human or other animal subjects. Administering DMSO and honey to the diseased portion of a nail will soften the diseased portion. In most instances, the un-diseased portion of the nail is not adversely affected by treatment with a DMSO-honey composition.

When used to treat diseased or damaged tissue, DMSO-honey compositions are more effective when applied at a temperature above 37 degree C. Warm applications are especially beneficial when treating musculoskeletal disorders, such as arthritis, sprains, strains, soft tissue injury and the like.

DMSO-honey compositions are also well suited for use with physical therapy techniques, particularly the use of energy such as ultra sound, in treating musculoskeletal disorders.

As illustrated by several examples below, DMSO-honey compositions soften and moisturize the skin of subjects receiving dermal applications. Certain DMSO-honey compositions accordingly make excellent cosmetic skin softening lotions or gels. Also DMSO-honey compositions are excellent as vehicles for other skin treating cosmetic agents. When the phrase "pharmaceutical compositions" is used herein, it thus includes cosmetic preparations.

Honey is known to have some beneficial effect on skin, but in most standard cosmetic compositions it may wash off. When DMSO and honey are used together, skin permeation of each is enhanced so the skin softening, and moisturizing benefits of honey are increased and sustained even after washing.

Formulations:

As with any multi-purpose pharmaceutical composition, some experimentation is necessary to determine the optimum dosage of DMSO and honey to be applied for a particular purpose. For example, when it is a goal to reduce a side-effect produced by the application of DMSO, the amount of honey, and/or sugar blends used should be an amount effective to obtain the desired reduction. Likewise, if the goal is to enhance the healing attributes of the honey, then the amount of honey should be increased to an amount sufficient to enhance these benefits, with the DMSO proportions reduced to allow additional skin penetration of the honey. I have experimented over the last three years with various formulations of DMSO and honey, with an excellent, general, formulation being 1 part honey, 7 parts DMSO, and 3 parts water. Likewise, the usage of sugar formulations, while somewhat effective, are not nearly as effective as is honey. Likewise, experimentation with sugar combinations alone, has not proven to be nearly as effective, and sometimes ineffective, in promoting wound healing, nor is the anti-bacterial effect as pronounced in the sugar combinations as it is with honey. Honey, alone, proved to be anti-fungal, whereas the sugar solutions did not prove to be so.

Over the last twenty five years the inventor has experimented with DMSO, and various formulations of it with other additives. It has been found that honey is the perfect, symbiotic additive for DMSO therapy, including orally ingested DMSO therapy. One of the popular additives, Aloe, spoils at room temperature- the suggested storage temperature for DMSO solutions, while the "Material Safety Data Sheet" for Urea, another additive, states that "direct contact with eyes and skin may cause irritation, redness, itching and pain. These negative factors are not present with honey. Additionally, urea, in its natural state, is derived from urine. This is a great psychological deterrent to its use. Honey, in all regards, physiologically and psychologically, is the best additive for DMSO therapy. This inventor has further experimented by injecting a slightly diluted solution of the preferred mixture with no ill effects and great positive therapeutic benefit.

As described in the prior patents listed above, DMSO compositions for topical application should contain at least 10 weight percent DMSO to have any beneficial effect. Compositions for clinical use should have at least about 40 weight percent DMSO; and for greatest effect, a composition should contain at least about 50 weight percent DMSO. To be effective in reducing DMSO-induced side effects and/or to enhance therapeutic actions, over that of DMSO, compositions alone, honey should be present in a weight or volume ratio to DMSO of greater than 1:99. Most significant results are achieved when the weight ratio of honey to DMSO is greater than eight percent honey to DMSO. Normally, DMSO-honey compositions should contain no more than about 60 weight percent honey since larger concentrations could only be obtained at the cost of reduced effectiveness due to diminished DMSO amounts, and the resultant stickiness of the honey residue. If this mixture/compilation is used with a dressing, such as in burn or wound healing, then this aspect does not apply and the ratio of honey to DMSO can be increased.

Compositions containing one weight percent or less of DMSO are effective for treating membranes that have been stressed, e.g. membranes that are inflamed, are scarified or have been submitted to severe osmotic stress. In such instances, the above stated DMSO-honey ratios would still apply.

Pharmaceutical compositions for treating the skin, oral cavity and rectal epithelium may contain DMSO and honey as their sole components. In any such composition, the weight ratio of DMSO to honey should not be less than about 5/1, and the honey rate can also be increased.

To facilitate topical applications, any of the above compositions may include a pharmaceutically acceptable thickening agent to increase the viscosity of a composition. Such thickeners may be used to form creams, lotions, gels, pastes, ointments and suppositories. Honey, alone, serves as a partial thickener.

Methods of Application

Honey may be administered with DMSO compositions orally, topically, or by injection. I.V. administration has not been studied. The most dramatic reductions in side-effects are observed when honey is added to DMSO compositions for topical application and oral ingestion. Subjects using topically applied DMSO suffer from substantially less malodorous breath, foul taste, and adverse skin reaction when honey is used along with the DMSO. The bad taste and bad breath caused by DMSO is substantially reduced in oral administration when honey is used in solution with the DMSO and the healing ability is enhanced.

Topical applications of DMSO and honey may be by any standard technique. They may be painted or spread on and allowed to dry or applied with saturated pads, or the fingers.

One advantageous method for treating limbs or digits is to place an appropriate DMSO-honey liquid composition in a plastic bag and insert the limb so that the bag forms an over-wrap. Heat can be applied to the exterior of the bag to accelerate treatment.

Similarly, spinal injuries can be treated by saturating a fabric with a DMSO-honey solution and then spreading the fabric along the spinal column. The fabric may be covered with a nonporous plastic sheet and hot water bottles applied to speed penetration of the DMSO-honey solution.

This also works effectively for wrapping the large joints, such as the knee or elbow. For rapid application, over smaller areas, the fingers can be dipped in the DMSO-honey solution and the solution rubbed over the effected area. If a thin coating is applied in this manner, after a couple of minutes, the areas can again be rubbed with the hands and a smooth silky feeling, with no stickiness, to the touch is presented. The application is thus dried and clothing can be worn immediately at that time.

In most instances, it is preferred that DMSO and honey be combined in a common composition for administration together or otherwise be administered concurrently. In the specific case of topically applied DMSO composition, some reduction in side-effects is also observed if patients are treated with DMSO without honey after a preceding treatment at the same site, with both DMSO and honey. For topical administrations at least, it is thus possible to use treatment regimens such as alternating applications of DMSO compositions with and without honey.

If a DMSO composition, for topical application, includes substances which would react adversely or be deactivated when combined with honey or would react with honey to form macromolecules which would retard tissue penetration, a honey composition can first be applied to the treatment site and allowed to dry. The DMSO composition could thereafter be applied at the same site with less chance that the honey-sensitive substances would be adversely affected.

As previously mentioned, alternating applications of a DMSO composition and a honey composition may be advisable under some circumstances. For example, in the unusual circumstance that a preferred DMSO composition contains a chemical agent that is unstable in the presence of honey, it would be preferable to alternate applications of the DMSO composition and a honey composition or to mix the two compositions immediately before administration. Sequential applications of DMSO and honey compositions or mixing immediately before application might also be preferred if the separate DMSO and honey compositions have a substantially longer shelf life than some combined formulation. Whether to combine honey with a particular DMSO composition is best determined by experimentation.

Applying honey over an area to be treated, with, or without dilution with water, and then applying DMSO to the area, is also a highly effective treatment.

References Supporting the Healing Benefits of Honey

The University of Waikato, New Zealand, Honey Research Unit 3.2. Honey as an Antiseptic Dressing
3.2.1 Established Usage of Honey as a Dressing Honey has a well established usage as a wound dressing in ancient and traditional medicine [10]. In recent times this has been re-discovered, and honey is in fairly widespread use as a topical antibacterial agent for the treatment of wounds, burns and skin ulcers, there being many reports of its effectiveness [11-23]. The observations recorded are that inflammation, swelling and pain are quickly reduced, unpleasant odors cease, sloughing of necrotic tissue occurs without the need for debridement, dressings can be removed painlessly and without causing damage to re-growing tissue, and healing occurs rapidly with minimal scarring, grafting being unnecessary. In many of the cases honey was used on infected lesions not responding to standard antibiotic and antiseptic therapy. It was found in almost all of the cases to be very effective in rapidly clearing up infection and promoting healing.

3.2.2. Importance of Antibacterial Activity

Much of the effectiveness of honey as a dressing appears to be due to its antimicrobial properties. The healing process will not occur unless infection is cleared from a lesion: swabbing of wounds dressed with honey has shown that the infecting bacteria are rapidly cleared [13,16,18,20,24]. In this respect honey is superior to the expensive modern hydrocolloid wound dressings as a moist dressing. Although tissue re-growth in the healing process is enhanced by a moist environment, and deformity is prevented if the re-growth is not forced down by a dry scab forming on the surface, moist conditions favor the growth of infecting bacteria. Antibiotics are ineffective in this situation, and antiseptics cause tissue damage, so slow the healing process [25]. Honey is reported to cause no tissue damage, and appears to actually promote the healing process. There are also numerous reports of sugar being used as a wound dressing, this also being found to be effective [23-31]. Antibacterial activity is attributed by several authors to the high osmolarity of the sugar or honey [11,17,22,27], it not being generally recognized that some honeys can have additional antibacterial activity considerably greater than that due to the osmolarity. This additional activity would be of particular significance in situations where the dressing becomes diluted by body fluids, and in regions of a lesion that are not in direct contact with the dressing. Staphylococcus aureus is exceptionally osmotolerant: for complete inhibition of its growth the $a_w$ has to be lowered below 0.86, which would be a typical honey at 29% (v/v). In the reports of sucrose syrup or paste being used as a wound dressing it is noted that infection with Staphylococcus aureus is hard to clear. Measurements that have been reported [27] of the dilution occurring from the uptake of water from surrounding tissues when an abdominal wound was packed with sugar reveal that a saturated sucrose syrup containing undissolved granules becomes diluted in 7.5 hours to a concentration that is 30% of that of a saturated solution. Although the $a_w$ of this solution is low enough to prevent the growth of most human pathogens, it is not low enough to seriously restrict the growth of Staphylococcus aureus, a species which has developed resistance to many antibiotics and has become the predominant agent of wound sepsis in hospitals [32]. But Staphylococcus aureus is one of the species most sensitive to the antibacterial activity of honey. There have been many reports of complete inhibition of Staphylococcus aureus by honeys diluted to much lower concentrations [4], showing the importance of the other antibacterial factors in selected honeys.

To know for certain the clinical significance of the additional antibacterial activity in honey, a clinical trial will need to be conducted to compare dressings of sugar and selected honeys. The little comparative work reported to date indicates that more rapid healing is achieved with honey than with sugar [12,15]. Since infection is one of the most common impediments to wound healing [33], then such results would be expected if the sugar dressing were not able to fully suppress the growth of bacteria as the sugar became diluted. The additional antibacterial activity of honey could be the reason for the remarkable rates of healing reported when honey has been used as a dressing [11,13,14].

3.2.3. Effectiveness against Wound-infecting Species of Bacteria

The seven species of bacteria most commonly involved in wound infection have been tested for their sensitivity to the antibacterial activity of honey [24]. The two major forms of antibacterial activity were examined separately: a honey with an average level of activity due to hydrogen peroxide and no detectable non-peroxide activity was used; also a manuka honey with an average level of non-peroxide activity, with catalase added to remove any hydrogen peroxide. The results of this study are summarized in Table 1.

Overall there was little difference between the two types of antibacterial activity in their effectiveness, although some species were more sensitive to the action of one type of honey than they were to the other. The results thus showed that these honeys, with an average level of activity, could be diluted nearly ten-fold yet still completely inhibit the growth of all the major wound-infecting species of bacteria. It is notable that the manuka honey, with an average level of activity, could be diluted with 54 times its volume of fluid yet still completely inhibit the growth of Staphylococcus aureus, the major wound-infecting species, and a species notorious for its development of resistance to antibiotics.

TABLE 1

The minimum concentration of honey (%, v/v) in the growth medium needed to completely inhibit the growth of various species of wound-infecting bacteria.

| Bacterial Species | Manuka honey | Other honey |
|---|---|---|
| Escherichia coli | 3.7 | 7.1 |
| Proteus mirabilis | 7.3 | 3.3 |
| Pseudomonas aeruginosa | 10.8 | 6.8 |
| Salmonella typhimurium | 6.0 | 4.1 |
| Serratia marcescens | 6.3 | 4.7 |
| Staphylococcus aureus | 1.8 | 4.9 |
| Streptococcus pyogenes | 3.6 | 2.6 |

There are frequent reports of hospital wards being closed because of the presence of strains of methicillin-resistant Staphylococcus aureus (MRSA). Because these strains are resistant to all of the antibiotics in common use it is necessary to protect patients with impaired immunity from exposure to them in case they contract infections which will not respond to treatment. The collection of strains of MRSA at Waikato Hospital have been tested for sensitivity to the two honeys described above [35]. All of the strains were found to be completely inhibited by both honeys at 10% (v/v) in the growth medium, and many of the strains by the honeys at 5% (v/v).

1. Dustmann J H. (1979) Antibacterial Effect of Honey. *Apiacta* 14, 7-11.
2. Majno G: *The Healing Hand Man and Wound in the Ancient World.* Harvard University Press Cambridge, Mass. 1975.
3. Ransome H M: *The Sacred Bee in Ancient Times and Folklore.* George Allen and Unwin London. 1937.
4. Molan P C. (1992) The Antibacterial Activity of Honey. 1. The Nature of the Antibacterial Activity. *Bee World* 73, 5-28.
5. Molan P C. (1992) The Antibacterial Activity of Honey. 2. Variation in the Potency of the Antibacterial Activity. Bee World 73, 59-76.
6. Aristotle (350 B.C.). Translated by Thompson DÕA W. *Historia Animalium in: The Works of Aristotle* (Smith J A, Ross W D editors) Oxford University Press Oxford 1910 Volume IV.
7. Gunther R T: *The Greek Herbal of Dioscorides* (Translated by Goodyear J, 1655). Hafner N. Y. 1934, reprinted 1959.
8. Allen K L, Molan P C, Reid G M. (1991) A Survey of the Antibacterial Activity of Some New Zealand Honeys. *J. Pharm. Pharmacol.* 43, 817-822.
9. Allen K L, Molan P C, Reid G M. (1991) The Variability of the Aantibacterial Activity of Honey. *Apiacta* 26, 114-121.
10. Zumla A, Lulat A. (1989) Honey—a Remedy Rediscovered. *J. Royal Soc. Med.* 82, 384-3.
11. Bulman M W. (1955) Honey as a Surgical Dressing. *Middlesex Hosp. J.* 55, 188-189.
12. Hutton D J. (1966) Treatment of Pressure Sores. *Nurs. Times* 62, 1533-1534.
13. Cavanagh D, Beazley J, Ostapowicz F. (1970) Radical Operation for Carcinoma of the Vulva. A New Approach to Wound Healing. *J. Obstet. Gynaecol. Br. Cmwlth.* 77, 1037-1.
14. Blomfield R. (1973) Honey for Decubitus Ulcers. *J. Am. Med. Assoc.* 224, 905.
15. Burlando F. (1978) Sull'azione Terapeutica del Miele nelle Ustioni. *Minerva Dermat.* 113, 699-706.
16. Armon P J. (1980) The Use of Honey in the Treatment of Infected Wounds. *Trop. Doct.* 10, 91.
17. Bose B. (1982) Honey or Sugar in Treatment of Infected Wounds? *Lancet i,* 963.
18. Dumronglert E. (1983) A Follow-up Study of Chronic Wound Healing Dressing with Pure Natural Honey. *J. Natl Res. Counc. Thail.* 15, 39-66.
19. Kandil A, Elbanby M, Abd-Elwahed K, Abou Sehly G, Ezzat N. (1987) Healing Effect of True Floral and False Nonfloral Honey on Medical Wounds. *J. Drug Res. (Cairo)* 17, 71-75.
20. Effem S E E. (1988) Clinical Observations on the Wound Healing Properties of Honey. *Br. J. Surg.* 75, 679-681.
21. Farouk A, Hassan T, Kashif H, Khalid S A, Mutawali I, Wadi M. (1988) Studies on Sudanese Bee Honey: Laboratory and Clinical Evaluation. *Int. J. Crude Drug Res.* 26, 161-168.
22. Green A E.(1988) Wound Healing Properties of Honey. *Br. J. Surg.* 75, 1278.
23. McInerney R J F. (1990) Honey—a Remedy Rediscovered. *J. Royal Soc. Med* 83, 127.

National Honey Board References:
Antioxidants

Generally, darker honeys and those with higher water content have stronger antioxidant potential. The antioxidants identified thus far in honey are pinocembrin, pinobanksin, chrysin and galagin.

Pinocembrin is unique to honey and found in the highest amount relative to the others. Ascorbic acid (vitamin C), catalase and selenium are also present.

Microbiology

Honey has inherent antimicrobial properties that discourage the growth or persistence of many microorganisms. The microbes that may be found in honey are primarily yeasts and spore-forming bacteria. No vegetative forms of disease-causing bacterial spores have been found in honey. Because bacteria do not replicate in honey, if high numbers of vegetative bacteria were to be detected, it may indicate contamination from a secondary source.

ZINC:
One of the many minerals contained in honey.
© National Honey Board
390 Lashley St., Longmont, CO 80501-6045
Phone: (303) 776-2337
Fax: (303) 776-1177
URL: http://www.nhb.org

I claim:

1. In a method of administering DMSO-d (dimethyl sulfoxide) for pharmacological applications to a host, in which a formulation consisting of DMSO is administered to said host, wherein the improvement comprises administering a formulation consisting essentially of a weight ratio of one part DMSO, and less than one part honey to said host; wherein the improved method of administration results in the potentiation of DMSO and the reduction of malodorous breath, bad taste, bad body odor, painful skin reactions, and itching normally associated with administration of formulations consisting of DMSO.

2. The method of administering DMSO according to claim 1 wherein said formulation further includes water.

3. The method of administering DMSO according to claim 1 wherein the weight ratio of honey to DMSO is greater than 1:99.

4. The method of administering DMSO according to claim 1 wherein the ratio of honey to DMSO is greater than 1.9.

5. The method of administering DMSO according to claim 1 wherein the ratio of honey to (DMSO) is greater than 1:7.

6. The method according to claim 1 wherein said formulation consists of the following components:

| | |
|---|---|
| dimethyl sulfoxide | about 19 grams; |
| honey | about 2 grams; |
| water | about 6 grams. |

7. In a method of formulating a DMSO solution for pharmacological applications to a host, in which a solution consisting of DMSO is administered to said host, wherein the improvement comprises formulating said DMSO solution such that it consists essentially of a weight ratio of one part DMSO, and less than one part honey; wherein the improved method of formulating DMSO results in the potentiation of DMSO and the reduction of malodorous breath, bad taste, bad body odor, painful skin reactions, and itching normally associated with administration of solutions and other formulations of DMSO to a host.

8. The method of formulating a DMSO solution for application to a host, according to claim 7, wherein said formulation also includes additives, such that the ratio of honey to DMSO, and or to DMSO plus other additives, is not more than 50% honey.

9. The method of administering a formulation of DMSO to a host, according to claim 1, wherein said formulation also includes additives, such that the ratio of honey to DMSO, and or to DMSO plus other additives, is not more than 50% honey.

10. The method of administering a formulation of DMSO to a host, according to claim 1, wherein said formulation consists of 40 to 90% DMSO, and 1 to 50% honey.

* * * * *